United States Patent
Tindale

(10) Patent No.: US 11,174,215 B2
(45) Date of Patent: Nov. 16, 2021

(54) METHOD OF PRODUCING METHYL METHACRYLATE OR METHACRYLIC ACID

(71) Applicant: Mitsubishi Chemical UK Limited, Billingham (GB)

(72) Inventor: Neil Tindale, Redcar (GB)

(73) Assignee: MITSUBISHI CHEMICAL UK LIMITED, Billingham (GB)

(*) Notice: Subject to any disclaimer, the term of this patent is extended or adjusted under 35 U.S.C. 154(b) by 0 days.

(21) Appl. No.: 16/496,695

(22) PCT Filed: Mar. 23, 2018

(86) PCT No.: PCT/GB2018/050759
§ 371 (c)(1),
(2) Date: Sep. 23, 2019

(87) PCT Pub. No.: WO2018/172783
PCT Pub. Date: Sep. 27, 2018

(65) Prior Publication Data
US 2020/0031754 A1  Jan. 30, 2020

(30) Foreign Application Priority Data
Mar. 24, 2017  (GB) .................................... 1704729

(51) Int. Cl.
*C07C 67/20* (2006.01)
*C07C 51/06* (2006.01)
*C07C 57/04* (2006.01)
*C07C 69/54* (2006.01)

(52) U.S. Cl.
CPC .............. *C07C 67/20* (2013.01); *C07C 51/06* (2013.01); *C07C 57/04* (2013.01); *C07C 69/54* (2013.01)

(58) Field of Classification Search
CPC ....... C07C 233/09; C07C 51/06; C07C 67/20; C07C 305/06; C07C 57/04; C07C 69/54; C07C 231/06; C07C 231/12; C07C 231/14; C07C 231/22; C07C 303/24; C07C 303/42; C07C 235/06; C07C 51/50; C07C 67/62; B01J 19/0026
See application file for complete search history.

(56) References Cited

U.S. PATENT DOCUMENTS

| | | | | |
|---|---|---|---|---|
| 3,006,900 A * | 10/1961 | Wilhelm | ............... | C08F 226/10 526/219.1 |
| 3,210,419 A | 10/1965 | McConnell | | |
| 4,529,816 A * | 7/1985 | DeColibus | ............... | C07C 67/20 560/212 |
| 5,554,792 A | 10/1996 | Sawayama et al. | | |
| 5,859,280 A * | 1/1999 | Arhancet | ................ | C07B 63/04 558/462 |
| 2003/0208093 A1* | 11/2003 | Carlson, Jr. | ............. | C07C 67/22 562/598 |
| 2006/0247377 A1* | 11/2006 | Riegel | ..................... | C07C 69/54 525/176 |
| 2016/0137590 A1 | 5/2016 | Bernardin et al. | | |

FOREIGN PATENT DOCUMENTS

| | | |
|---|---|---|
| EP | 0561264 A2 | 3/1993 |
| JP | 2001106708 A | 4/2001 |
| RU | 2472770 C2 | 1/2013 |
| WO | 03016263 A1 | 2/2003 |
| WO | 2015140549 A1 | 9/2015 |

OTHER PUBLICATIONS

CAS (One page, published 2020) (Year: 2020).*
CAS 787-07-5 (Year: 2020).*
International Search Report and Written Opinion for application No. PCT/GB2018/050759; dated Jun. 18, 2018; 11 pages.
International Preliminary Report on Patentability for Application No. PCT/GB2018/050759; 9 pages; dated Sep. 24, 2019.
Great Britain Search Report for Application No. GB 1704729.1; dated Jan. 11, 2018; 5 pages.
Russia; English Translation of Search Report cited in Russian Application No. 2019133652; dated Mar. 6, 2021; 2 Pages.
Russia; English Translation of Office Action related to Russian Application No. 2019133652; dated Jun. 3, 2021; 6 Pages.

* cited by examiner

*Primary Examiner* — Jafar F Parsa
*Assistant Examiner* — Blaine G Doletski
(74) *Attorney, Agent, or Firm* — Shumaker, Loop & Kendrick, LLP

(57) ABSTRACT

There is described a method of reducing polymer tar build-up in the production of methyl methacrylate and/or methacrylic acid by the acetone cyanohydrin process. In the method a stabiliser is contacted with the amide stage reaction medium. The stabiliser includes a hydrocarbon moiety capable of donating a labile hydrogen atom to a methacrylamide derivative capable of reaction with said labile hydrogen atom under the conditions in the said medium. The method herein is especially useful for the continuous production of methyl methacrylate and/or methacrylic acid.

7 Claims, No Drawings

METHOD OF PRODUCING METHYL METHACRYLATE OR METHACRYLIC ACID

CROSS REFERENCE TO RELATED PATENT APPLICATIONS

This application claims the benefit of and priority to PCT/GB2018/050759 filed Mar. 23, 2018 which claims the benefit of and priority to Great Britain Application No. 1704729.1 filed on Mar. 24, 2017.

TECHNICAL FIELD AND BACKGROUND IN THE INVENTION

The present invention relates to a method for reducing tar-like build-up during the production of methyl methacrylate ("MMA") or methacrylic acid ("MAA") using the acetone cyanohydrin (ACH) process.

A number of commercial processes are used to prepare MMA. In one such process MMA is prepared from acetone cyanohydrin ("ACH"). An example of this process is described in U.S. Pat. No. 4,529,816. Generally, in the ACH process ACH is dissolved in, and hydrolysed by, an excess of concentrated sulphuric acid to produce in solution a mixture of Sulphatoisobutyramide ("SIBAM") and Hydroxyisobutyramide ("HIBAM"). While still in the form of a solution in concentrated sulphuric acid, the HIBAM and SIBAM are thermally converted to methacrylamide ("MAM") plus a small amount of Methacrylic Acid ("MAA"). From the initial mixing of ACH with concentrated sulphuric acid to the end of the thermal conversion of SIBAM plus HIBAM to MAM, these process steps are collectively known as the "amide stage" of the process.

If the desired end product of the process is MAA, then the product of the amide stage of the process, being a concentrated sulphuric acid solution of MAM, is mixed with water, whereupon MAA is produced via hydrolysis of the MAM. If the desired product is MMA, the concentrated sulphuric acid solution of MAM is mixed with water and methanol, whereupon MMA is produced via a combination of hydrolysis and esterification of the MAM.

The acetone cyanohydrin route to MMA or MAA is typically engineered as a continuous process, with output in the region of between 10 and 20 to/hr.

In order to facilitate the thermal conversion of SIBAM plus HIBAM to MAM, both heat and residence time must be provided. A decrease in thermal conversion to the desired MAM results in a decreased overall yield for the process, and so high temperatures and relatively long residence times are typically used. Unfortunately, undesirable by-products are also formed in the amide stage of the process, and particularly in the high temperature thermal conversion stage. The undesirable by-products are made up of a wide range of chemical components, including many sulfonated compounds and also some oligomeric and polymeric materials.

The non-aqueous solvent properties of concentrated sulphuric acid are such that throughout the amide stage of the process, the undesirable by-products remain dissolved in the reaction solution. However, when the reaction solution passes on into the hydrolysis (for MAA) or esterification (for MMA) process stages, water or water plus methanol must be added to bring about the desired chemical conversion. The addition of water or water plus methanol causes the properties of the solvent medium to change significantly, as a highly acidic aqueous medium is formed from a previously non-aqueous one. In this new solvent environment, any components which may have been soluble in the concentrated sulphuric acid but which are largely insoluble in the new medium will precipitate from the solution, potentially forming small droplets or even solid particles. A process of agglomeration of the small droplets or solid particles may take place, so that larger droplets and particles eventually form deposits on the process reaction vessels, process equipment and pipework.

The solid deposit material is typically referred to as "polymer tar" or just "tar". The tar is a viscous, sticky solid, and if untreated this will accumulate in process vessels, process equipment and pipe-work. Blockage of process equipment in the hydrolysis or esterification stages of the acetone cyanohydrin process occurs when accumulation of a sufficiently large amount of tar has taken place. The blockages are difficult to remove by conventional means such as pumping, chemical cleaning or dissolving The hydrolysis or esterification process steps of the ACH process generate MAA or MMA respectively, which may be recovered from the sulphuric acid reaction solution by processes such as liquid-liquid separation, distillation or steam stripping, to form a crude product which may then be subjected to further purification to produce a commercially pure product. After the recovery of crude MAA or MMA is complete, the remaining sulphuric acid containing mixture is known by those skilled in the art as "spent acid", or "by-product acid". Due to the relatively large volumes of spent acid produced from the acetone cyanohydrin route to MAA or MMA, and the relatively high cost of fresh sulphuric acid, the spent acid from the acetone cyanohydrin route to MAA or MMA is typically recycled in a separate process step known as a Sulphuric Acid Recovery ("SAR") process.

Typical SAR processes are described in EP1057781 and U.S. Pat. No. 5,531,169, which both disclose SAR processes where the spent acid is introduced into a furnace in the form of aerosol droplets, along with fuel and air or oxygen. The fuel/air mixture is combusted to generate the necessary heat to vaporise, dissociate and decompose the acid along with any contaminants that may also be present to form a gas stream made up of mainly water, carbon dioxide, nitrogen and sulphur dioxide. The sulphur dioxide may then be converted back to concentrated sulphuric acid in subsequent process steps.

The aerosol droplets are typically produced in the SAR furnace by using a number of spray guns. The throughput of each of the spray guns is limited, and so a sufficient number of working spray guns must be provided to allow the processing of the complete volume of spent acid from the hydrolysis or esterification reaction to be managed.

Generally the spray guns work by forcing the liquid spent acid through a small diameter orifice under pressure. Unfortunately, the presence of polymer or other solid materials in the spent acid feed stream can block up the spray gun orifice, preventing further operation of the spray guns and thus causing a reduction in the rate at which the spent acid can be processed.

On sites where the processing rate of spent acid is the factor which limits the rate of production of MAA or MMA, then any limitation on spent acid processing rate will cause a reduction to the rate of production of useful commercial products. As a consequence there will be a financial loss to the organisation.

For both economic and safety reasons the avoidance of formation and accumulation of significant deposits of tar is highly desirable.

Previous attempts at tar removal have been managed by stopping the process, which is otherwise continuous, followed by draining, decontamination and cleaning by mechanical means, for example U.S. Pat. No. 6,245,216, which discloses the use of strong acids plus surfactants in combination with agitation to achieve a tar liquification effect. Such stoppages for clean-downs may take between 1 and 5 days to accomplish, and because the process is otherwise continuous, producing many tonnes per hour of product, any stoppage represents a significant loss of earning potential. The clean-down stoppages are also undesirable because of the potential for exposure of those taking part in the clean-down activity to harmful sulphuric acid containing process liquid.

Stabilisers, such as polymerisation inhibitors, have also been used to try to prevent the formation of the undesired side products. For some time, the most widely deployed stabiliser has been phenothiazine ('PTZ'). However, Phenothiazine is a toxic crystalline material, and must be dissolved in a suitable solvent to facilitate its accurate addition to the process and uniform dispersion within the process. Suitable solvents include acetone, which is highly flammable and in which it is only sparingly soluble, or concentrated sulphuric acid, which is corrosive and harmful and in which solution it slowly degrades losing effectiveness even at ambient temperature.

Handling solid PTZ and dissolving it in suitable solvents introduces a potentially hazardous step to the process, and one which must be engineered with expensive layers of protection for the operatives to protect them from toxic PTZ dust and flammable or corrosive solvents.

Operators of large scale continuous chemical plants are typically reluctant to add any new chemicals into their processes, because of the number of significant risks that this introduces such as the new chemical additive taking part in undesirable side-reactions with other components that are present; the new chemical additive decomposing in such a way that the desired product of the process may become contaminated with a new trace impurity; the reaction mix foaming; and/or the new chemical causing corrosion or other damage to the process equipment.

For these reasons it has long been an aim of those operating the process to find more effective and more user friendly methods for reducing undesired side-products in the ACH process.

It is therefore an object of aspects of the present invention to address one or more of the above-mentioned, or other, problems. More specifically, it is an object of the present invention to provide a method for reducing tar build-ups and/or other undesired side-products during the ACH process for MMA and MAA production.

BRIEF SUMMARY OF THE INVENTION

According to a first aspect of the present invention there is provided a method of reducing polymer tar build-up in the production of methyl methacrylate and/or methacrylic acid by the acetone cyanohydrin process; wherein a stabiliser is contacted with the amide stage reaction medium, which stabiliser includes a hydrocarbon moiety capable of donating a labile hydrogen atom to a methacrylamide derivative capable of reaction with said labile hydrogen atom under the conditions in the said medium.

In the production of methyl methacrylate and/or methacrylic acid with the ACH process ACH is dissolved in, and hydrolysed by, an excess of concentrated sulphuric acid to produce in solution a mixture of Sulphatoisobutyramide ("SIBAM") and Hydroxyisobutyramide ("HIBAM"). While still in the form of a solution in concentrated sulphuric acid, the HIBAM and SIBAM are thermally converted to methacrylamide ("MAM") plus a small amount of MAA. From the initial mixing of ACH with concentrated sulphuric acid to the end of the thermal conversion of SIBAM plus HIBAM to MAM, these process steps are collectively known as the "amide stage" of the process.

It is surprising that the stabilisers of the present invention enable high amounts of MAM to remain in the monomer form despite the presence of concentrated sulphuric acid in the reaction medium.

The term 'concentrated sulphuric acid' herein may be defined as containing at least 93% w/w sulphuric acid and up to 7% w/w water. Preferably, the concentrated sulphuric acid in which the stabiliser is capable of donating a labile hydrogen atom to a methacrylamide derivative is in the form of an amide stage reaction medium. In the amide stage reaction medium, sulphuric acid may comprise at least 93% w/w of the solvent and the water content may be up to 7% w/w.

According to a second aspect of the present invention there is provided a method of producing methyl methacrylate or methacrylic acid comprising the steps of:
  a. contacting acetone cyanohydrin (ACH) with an excess of concentrated sulphuric acid to produce a mixture of sulphatoisobutyramide (SIBAM), hydroxyisobutyramide (HIBAM) and optionally methacrylamide; and
  b. thermally converting SIBAM and/or HIBAM to methacrylamide in concentrated sulphuric acid medium; and
  c. contacting the methacrylamide with water or with water and methanol;
wherein a stabiliser is present during step b, preferably during steps a and b, which stabiliser is added as a hydrocarbon moiety capable of donating a labile hydrogen atom to a methacrylamide derivative capable of reaction with said labile hydrogen atom under the conditions in the said medium.

Suitably, the method of the second aspect is a method for reducing tar build-up in the ACH production of MAA and/or MMA. Preferably, a method for reducing the production of tar components during the amide stage of the ACH process.

According to a further aspect of the present invention there is provided a reaction system comprising a mixture of:
  i. one or more of methacrylamide, sulphatoisobutyramide and hydroxyisobutyramide;
  ii. concentrated sulphuric acid; and
  iii. a stabiliser which includes a hydrocarbon moiety capable of donating a labile hydrogen atom to a methacrylamide derivative capable of reaction with said labile hydrogen atom under the conditions in concentrated sulphuric acid medium.

According to a further aspect of the present invention there is provided the use of a stabiliser in the production of methacrylic acid and/or methyl methacrylate by the acetone cyanohydrin (ACH) process, wherein the stabiliser includes a hydrocarbon moiety capable of donating a labile hydrogen atom to a methacrylamide derivative capable of reaction with said labile hydrogen atom under the conditions in concentrated sulphuric acid medium.

DETAILED DESCRIPTION OF THE INVENTION

The stabilisers of the present invention may be termed hydrogen transfer agents in that under the conditions found in the amide stage of the ACH process they are capable of taking part in a hydrogen atom transfer reaction, wherein a hydrogen atom is transferred to a chemically reactive species in the same medium, and in so doing prevents some or all of the side reactions that the species could otherwise take part in.

The labile hydrogen of the present invention may typically be attached to a tertiary carbon, or a secondary carbon which may in any case be acyclic or alicyclic. In preferred embodiments, there may be 2 or more such labile hydrogens. For the avoidance of doubt, labile hydrogen atoms are not attached to aromatic ring atoms.

The stabiliser added may be according to Formula I:

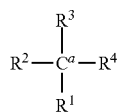

Formula I wherein $C^a$ is a carbon atom;

$R^1$ is hydrogen;

$R^2$ is hydrogen or is selected from optionally substituted aliphatic, aryl, araliphatic, aliphaticaryl, heteroaliphatic, heteroaryl, heteroaraliphatic, and heteroaliphaticaryl; preferably hydrogen, optionally substituted alkyl, alkenyl, alkynyl, alicyclic, aryl, aralkyl, alkaryl, heteroalkyl, heteroalkenyl, heteroalkynyl, heteroalicyclic, heteroaryl, heteroaralkyl, and heteroalkaryl; suitably hydrogen or optionally substituted $C_1$ to $C_{50}$ alkyl, $C_1$ to $C_{30}$ alkyl, $C_1$ to $C_{25}$ alkyl, $C_1$ to $C_{20}$ alkyl, $C_1$ to $C_{17}$ alkyl, $C_6$ to $C_{15}$ aryl, $C_6$ to $C_{10}$ aryl, $C_7$ to $C_{15}$ alkaryl or aralkyl; most preferably hydrogen or $C_1$ to $C_{10}$ alkyl;

$R^3$ is selected from optionally substituted aliphatic, aryl, araliphatic, aliphaticaryl, heteroaliphatic, heteroaryl, heteroaraliphatic, and heteroaliphaticaryl; such as optionally substituted alkyl, alkenyl, alkynyl, alicyclic, aryl, aralkyl, alkaryl, heteroalkyl, heteroalkenyl, heteroalkynyl, heteroalicyclic, heteroaryl, heteroaralkyl, and heteroalkaryl; suitably optionally substituted $C_1$ to $C_{50}$ alkyl, $C_1$ to $C_{30}$ alkyl, $C_1$ to $C_{25}$ alkyl, $C_1$ to $C_{20}$ alkyl, $C_1$ to $C_{17}$ alkyl, $C_6$ to $C_{15}$ aryl, $C_6$ to $C_{10}$ aryl, $C_7$ to $C_{15}$ alkaryl, $C_7$ to $C_{15}$ aralkyl or $C_7$ to $C_{15}$ heteroaralkyl;

$R^4$ is selected from is selected from optionally substituted aliphatic, aryl, araliphatic, aliphaticaryl, heteroaliphatic, heteroaryl, heteroaraliphatic, heteroaliphaticaryl or a group according to Formula II; such as optionally substituted alkyl, alkenyl, alkynyl, alicyclic, aryl, aralkyl, alkaryl, heteroalkyl, heteroalkenyl, heteroalkynyl, heteroalicyclic, heteroaryl, heteroaralkyl, heteroalkaryl or a group according to Formula II; suitably optionally substituted $C_1$ to $C_{50}$ alkyl, $C_1$ to $C_{30}$ alkyl, $C_1$ to $C_{25}$ alkyl, $C_1$ to $C_{20}$ alkyl, $C_1$ to $C_{17}$ alkyl, $C_6$ to $C_{15}$ aryl, $C_6$ to $C_{10}$ aryl, $C_7$ to $C_{15}$ alkaryl, aralkyl, or a group according to Formula II;

wherein two or more of $R^2$ to $R^6$, when present, may together, optionally with $C^a$ and/or $C^b$, when present, form a composite group, the composite group may be a monocyclic or polycyclic group and in this case, $R^2$ to $R^6$ may be taken to be a divalent equivalent of the groups defined herein;

with, in any of the above cases, the optional proviso that the stabiliser has a boiling point of ≥140° C. under the conditions of the reaction, preferably, the stabiliser has a boiling point of ≥140° C., more preferably ≥150° C. or ≥155° C., or ≥160° C. at a pressure of 1 bara, wherein Formula II is according to:

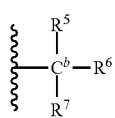

Formula II wherein $C^b$ is a carbon atom;

$R^7$ is hydrogen; and $R^5$ and $R^6$ are independently selected from hydrogen or optionally substituted alkyl, alkenyl, alkynyl, alicyclic, alkaryl, heteroalkyl, heteroalkenyl, heteroalkynyl, heteroalicyclic, and heteroalkaryl, and are preferably independently selected from hydrogen or optionally substituted alkyl, alicyclic, heteroalkyl and heteroalicyclic; suitably hydrogen, optionally substituted $C_1$ to $C_{50}$ alkyl, $C_1$ to $C_{30}$ alkyl, $C_1$ to $C_{25}$ alkyl, $C_1$ to $C_{20}$ alkyl, or $C_1$ to $C_{17}$ alkyl; preferably at least one of $R^5$ and $R^6$ is hydrogen, more preferably $R^5$ is hydrogen and $R^6$ is optionally substituted $C_1$ to $C_{50}$ alkyl, $C_1$ to $C_{30}$ alkyl, $C_1$ to $C_{25}$ alkyl, $C_1$ to $C_{20}$ alkyl, or $C_1$ to $C_{17}$ alkyl.

In an embodiment of a stabiliser according to Formula I: $R^4$ is a group according to Formula II and $R^5$ and $R^6$ are independently selected from hydrogen or optionally substituted alkyl, alicyclic, heteroalkyl and heteroalicyclic; suitably hydrogen, optionally substituted $C_1$ to $C_{50}$ alkyl, $C_1$ to $C_{30}$ alkyl, $C_1$ to $C_{25}$ alkyl, $C_1$ to $C_{20}$ alkyl, or $C_1$ to $C_{17}$ alkyl; preferably at least one of $R^5$ and $R^6$ is hydrogen, more preferably $R^5$ is hydrogen and $R^6$ is optionally substituted $C_1$ to $C_{50}$ alkyl, $C_1$ to $C_{30}$ alkyl, $C_1$ to $C_{25}$ alkyl, $C_1$ to $C_{20}$ alkyl, or $C_1$ to $C_{17}$ alkyl; and $R^2$ and $R^3$ are independently selected from hydrogen, optionally substituted alkyl, alkenyl, alkynyl alicyclic, heteroalkyl, heteroalkenyl, heteroalkynyl and heteroalicyclic; suitably optionally substituted alkyl, alicyclic, heteroalkyl, and heteroalicyclic; preferably hydrogen, optionally substituted $C_1$ to $C_{50}$ alkyl, $C_1$ to $C_{30}$ alkyl, $C_1$ to $C_{25}$ alkyl, $C_1$ to $C_{20}$ alkyl or $C_1$ to $C_{17}$ alkyl.

Preferably, in some embodiments in the stabiliser according to Formula I, when $R^2$ is hydrogen and $R^3$ has <7 non-hydrogen atoms, then $R^3$ and $R^4$ together contain ≥7 atoms selected from carbon and sulphur, suitably ≥$C_7$, with the proviso that when $R^4$ is Formula II then $R^3$ together with Formula II together contain ≥7 atoms selected from carbon and sulphur, suitably ≥$C_7$.

In the stabiliser according to Formula I, $R^2$ may be hydrogen when $R^3$ and $R^4$, together with $C^a$, form a monocyclic or polycyclic composite group, or when $R^4$ is Formula II then $R^2$ may be hydrogen when $R^3$ and $R^5$ and/or $R^6$ together with $C^a$ and $C^b$ form a monocyclic or polycyclic composite group.

In a preferred embodiment of a stabiliser according to Formula I, $C^a$ is a tertiary carbon atom, more preferably $C^a$ is a tertiary carbon atom that is not contained within a ring, and:

$R^4$ is a group according to Formula II and $R^5$ and $R^6$ are independently selected from hydrogen or optionally substituted alkyl, alicyclic, heteroalkyl and heteroalicyclic; suitably hydrogen, optionally substituted $C_1$ to $C_{50}$ alkyl, $C_1$ to $C_{30}$ alkyl, $C_1$ to $C_{25}$ alkyl, $C_1$ to $C_{20}$ alkyl, or $C_1$ to $C_{17}$ alkyl; preferably at least one of $R^5$ and $R^6$ is hydrogen, more preferably $R^5$ is hydrogen and $R^6$ is optionally substituted $C_1$ to $C_{50}$ alkyl, $C_1$ to $C_{30}$ alkyl, $C_1$ to $C_{25}$ alkyl, $C_1$ to $C_{20}$ alkyl, or $C_1$ to $C_{17}$ alkyl; and $R^2$ and $R^3$ are independently selected from hydrogen, optionally substituted alkyl, alkenyl, alkynyl alicyclic, heteroalkyl, heteroalkenyl, heteroalkynyl and heteroalicyclic; suitably optionally substituted alkyl, alicyclic, heteroalkyl, and heteroalicyclic; preferably hydrogen, optionally substituted $C_1$ to $C_{50}$ alkyl, $C_1$ to $C_{30}$ alkyl, $C_1$ to $C_{25}$ alkyl, $C_1$ to $C_{20}$ alkyl or $C_1$ to $C_{17}$ alkyl.

In a further preferred embodiment of a stabiliser according to Formula I:

$R^1$ and $R^2$ are hydrogen;

$R^3$ is selected from optionally substituted aryl, araliphatic, alkenyl alkynyl, heteroaryl, heteroaraliphatic, heteroalkenyl and heteroalkynyl, wherein for alkenyl alkynyl, heteroalkenyl and heteroalkynyl an unsaturated carbon is bonded to $C_a$, preferably $R^3$ is selected from optionally substituted aryl, including carbonyl substituted aryl, aralkyl heteroaryl or heteroaralkyl; suitably optionally substituted $C_6$ to $C_{15}$ aryl, $C_6$ to $C_{10}$ aryl, $C_7$ to $C_{15}$ aralkyl, or $C_7$ to $C_{11}$ aralkyl; and $R^4$ is selected from optionally substituted aliphatic, aryl, araliphatic, aliphaticaryl, heteroaliphatic, heteroaryl, heteroaraliphatic, and heteroaliphaticaryl; preferably optionally substituted alkyl, alkenyl, alkynyl, alicyclic, aryl, aralkyl, alkaryl, heteroalkyl, heteroalkenyl, heteroalkynyl, heteroalicyclic, heteroaryl, heteroaralkyl, and heteroalkaryl; and more preferably optionally substituted alkyl, alkenyl, alkynyl, aryl, aralkyl, heteroalkyl, heteroalkenyl, heteroalkynyl, heteroaryl, heteroaralkyl, even more preferably optionally substituted alkenyl, alkynyl, aryl, araliphatic, heteroalkenyl, heteroalkynyl, heteroaryl, heteroaraliphatic, wherein for alkenyl, alkynyl, heteroalkenyl and heteroalkynyl an unsaturated carbon is bonded to $C_a$; most preferably $R^4$ is selected from optionally substituted aryl, aralkyl, heteroaryl or heteroaralkyl; suitably optionally substituted $C_6$ to $C_{15}$ aryl, $C_6$ to $C_{10}$ aryl, $C_7$ to $C_{15}$ aralkyl, or $C_7$ to $C_{11}$ aralkyl.

In another preferred embodiment of the stabiliser according to Formula I, $R^3$ is selected from optionally substituted aralkyl or heteroaralkyl, $R^4$ is selected from optionally substituted aryl or heteroaryl and $R^3$ and $R^4$ together with $C^a$ form a polycyclic composite group. More preferably, in this embodiment $R^3$ is optionally substituted $C_7$ to $C_{15}$ aralkyl and $R^4$ is optionally substituted $C_6$ to $C_{15}$ aryl, and even more preferably $R^3$ is optionally substituted $C_7$ to $C_{11}$ aralkyl and $R^4$ is optionally substituted $C_6$ to $C_{10}$ aryl.

Accordingly, Formula I contains at least one labile hydrogen atom $R^1$, optionally $R^2$, when hydrogen and optionally $R^7$ when $R^4$ is a group according to Formula II.

In the case of stabiliser according to Formula I wherein one or more of $R^2$ to $R^4$ is an aryl group or contains unsaturated carbon-carbon bond directly attached to $C^a$ then when the labile hydrogen bonded to $C^a$ is lost the $C^a$ atom can be stabilised by the increased resonance effect within the molecule that results from the presence of a directly attached alkenyl, alkynyl or aryl structure.

In the case of stabilisers according to Formula I when $R^4$ is a group according to Formula II and therefore a carbon atom adjacent to $C^a$ comprises a labile hydrogen atom, energetic incentive for the hydrogen transfer reaction to take place can be gained by a subsequent process of transferring a second hydrogen atom from the adjoining carbon. Such stabilisers may be able to adopt a more stable structure after transfer of the labile hydrogen on the $C^a$ carbon via the loss of the second hydrogen from the adjacent carbon, $C^b$, and the subsequent formation of a double bond between the $C^a$ and the adjacent carbon, $C^b$.

Should $R^2$ to $R^4$ comprise aliphatic, alkyl and/or alicyclic groups, then when the labile hydrogen bonded to $C^a$ is lost the resulting intermediate can be stabilised by an inductive charge donation effect that may result from the presence and nature of the immediate substituent groups. These substituents may exert such a charge donation inductive effect as a result of their intrinsic electron rich or polarisable nature.

By the term "tertiary carbon" it is meant a carbon atom bonded to three other carbon atoms. By the term "secondary carbon" it is meant a carbon atom bonded to two other carbon atoms.

The term aliphatic herein means a hydrocarbon moiety that may be straight chain, branched or cyclic, and may be completely saturated, or contain one or more units of unsaturation, but which is not aromatic. The term "unsaturated" means a moiety that has one or more double and/or triple bonds. The term "aliphatic" is therefore intended to encompass alkyl, alicyclic, alkenyl or alkynyl groups. An aliphatic group preferably contains 1 to 50 carbon atoms, such as 1 to 30 carbon atoms, 1 to 25 carbon atoms, that is, an aliphatic group with 1, 2, 3, 4, 5, 6, 7, 8, 9, 10, 11, 12, 13, 14, 15, 16, 17, 18, 19, 20, 21, 22, 23, 24 or 25 carbon atoms. Preferably, an aliphatic group contains 1 to 25 carbons atoms, such as 1 to 20, 1 to 17 or 2 to 10 carbon atoms.

An alkyl group preferably contains 1 to 50 carbon atoms. Alkyl groups may be a straight or branched chain. The alkyl group preferably contains 1 to 30 carbon atoms, 1 to 25 carbon atoms, that is, an alkyl group with 1, 2, 3, 4, 5, 6, 7, 8, 9, 10, 11, 12, 13, 14, 15, 16, 17, 18, 19, 20, 21, 22, 23, 24 or 25 carbon atoms. Preferably, an alkyl group contains 1 to 25 carbons atoms, such as 1 to 20, 1 to 17 or 1 to 10 carbon atoms. Specifically, examples of an alkyl group include methyl, ethyl, n-propyl, iso-propyl, n-butyl, iso-butyl, sec-butyl, tert-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, 1,1-dinnethylpropyl, 1,2-dinnethylpropyl, 2,2-dinnethylpropyl, 1-ethylpropyl, n-hexyl, 1-ethyl-2-methylpropyl, 1,1,2-trinnethylpropyl, 1-ethylbutyl, 1-methylbutyl, 2-methylbutyl, 1,1-dimethylbutyl, 1,2-dinnethylbutyl, 2,2-dimethylbutyl, 1,3-dinnethylbutyl, 2,3-dimethylbutyl, 2-ethylbutyl, 2-methylpentyl, 3-methylpentyl and the like, and isomers thereof.

Alkenyl and alkynyl groups each preferably contain 2 to 50 carbon atoms, such as 2 to 30 carbon atoms, 2 to 25 carbons atoms, such as 2 to 20, 2 to 17 or 2 to 10 carbon atoms. Such groups may also contain more than one carbon-carbon unsaturated bond. Alkenyl groups may be a straight or branched chain.

Alicyclic groups may be saturated or partially unsaturated cyclic aliphatic monocyclic or polycyclic (including fused, bridging and spiro-fused) groups which have from 3 to 50 carbon atoms, such as 3 to 30 carbon atoms or 3 to 25 carbon atoms, that is an alicyclic group with 3, 4, 5, 6, 7, 8, 9, 10, 11, 12, 13, 14, 15, 16, 17, 18, 19, 20, 21, 22, 23, 24 or 25 carbon atoms. Preferably, an alicyclic group has from 3 to 20, more preferably from 3 to 17, even more preferably from 3 to 12, even more preferably from 3 to 10 carbon atoms, even more preferably from 3 to 6 carbons atoms. The term "alicyclic" encompasses cycloalkyl, cycloalkenyl and cycloalkynyl groups. It will be appreciated that the alicyclic group may comprise an alicyclic ring bearing one or more linking or non-linking alkyl substituents, such as —$CH_2$-cyclohexyl. Specifically, examples of $C_{3-20}$ cycloalkyl groups include cyclopropyl, cyclobutyl, cyclopentyl, cyclohexyl, cycloheptyl, adamantyl, isobornyl and cyclooctyl.

An aryl group is a monocyclic or polycyclic group having from 5 to 50 carbon atoms, such as 6 to 30 carbon atoms, 6 to 25, 6 to 20, or 6 to 15 carbon atoms, or 6 to 12 carbon atoms, such as 6 to 10 carbon atoms. An aryl group is preferably a "$C_{6-12}$ aryl group" and is an aryl group constituted by 6, 7, 8, 9, 10, 11 or 12 carbon atoms and includes condensed ring groups such as monocyclic ring group, or bicyclic ring group and the like. Specifically, examples of "$C_{6-10}$ aryl group" include phenyl, biphenyl, indenyl, naphthyl or azulenyl and the like. It should be noted that condensed rings such as indan and tetrahydro naphthalene are also included in the aryl group.

Groups containing more than one type of moiety, such as a first moiety and a second moiety, specifically araliphatic, aliphaticaryl, aralkyl and alkaryl herein mean that the group contains both types of moiety. For example, an "araliphatic" group contains an aryl moiety and an aliphatic moiety. Such groups are attached to $C_a$ or $C_b$ via the first named moiety, for example for "araliphatic" via the aryl moiety, and the second named moiety is a substituent on the first moiety, for example for "araliphatic" an aliphatic group is a substituent on the aryl group. Such groups may comprise one or more substituents according to the second moiety, for example for "araliphatic", more than one aliphatic substituent may be present on the aryl moiety. For the avoidance of doubt, the term aliphaticaryl means an aryl substituted aliphatic group.

When a stabiliser of the present invention comprises one or more monocyclic and/or polycyclic groups, said cyclic groups may include one or more alicyclic and/or aromatic rings. Said groups may also be bi- or tri- or polycyclic. For the avoidance of doubt, $C^a$ may also be a cyclic atom contained within a ring in the stabiliser of the present invention.

The use of the term "hetero" in heteroaliphatic, heteroaryl, heteroaraliphatic, heteroaliphaticaryl; heteroalkyl, heteroalkenyl, heteroalkynyl, heteroalicyclic, heteroaralkyl, heteroalkaryl and the like is well known in the art. Heteroaliphatic, heteroaryl, heteroaraliphatic, heteroaliphaticaryl; heteroalkyl, heteroalkenyl, heteroalkynyl, heteroalicyclic, heteroaralkyl, heteroalkaryl refers to an aliphatic, aryl, araliphatic, aliphaticaryl; alkyl, alkenyl, alkynyl, alicyclic, aralkyl, alkaryl group, as defined herein, wherein one or more carbon atoms has been replaced by a heteroatom in the chain and/or ring of the group, as applicable, respectively. The heteroatom(s) may be one or more of sulphur, oxygen and/or nitrogen.

The heteroatom(s) may be in any form that does not remove the hydrogen donating function of the stabiliser. In particular, it has been found that a broad range of heteroatom-containing groups attached to atoms other than those directly bonded to the $C^a$ carbon may be tolerated. It will be appreciated that the environment of concentrated sulphuric acid may result in chemical modification to the stabiliser in situ. However, such stabiliser still falls within the present invention as long as the modified stabiliser retains the hydrogen donating functionality.

The heteroatom(s) may be in the form of an ether group; if terminal, a hydroxyl group; an amine or amide, more preferably, a secondary amine, such as a secondary amine in a ring; nitrogen, sulphur and oxygen heterocycles; and/or a polysulphide group in the carbon backbone, such as a polysulphide containing at least three sulphur atoms. Generally, $R^2$ to $R^6$ may in total include up to several heteroatoms in the carbon chains or as substituent hydroxyl, carbonyl or carboxyl oxygens, more typically, up to four hetero atoms, most typically, 1, 2 or 3 heteroatoms present as carbonyl oxygen substituents or contained within carbon chains or rings and therefore relatively inert. Most preferred are heteroatoms present as oxygen and nitrogen containing heterocycles, sulphur containing chains or carbonyl substituent oxygen atoms, preferably in the form of a ketone group. Such heteroatom-containing groups have been found in particular to be stable. Preferably, a heteroatom is not directly bonded to the $C^a$ atom, more suitably a heteroatom is spaced by at least two carbon atoms from the $C^a$ atom.

By the term "optionally substituted" at the start of a list of chemical species is meant that all of the species in the list which can be substituted may be optionally substituted; that is it is not meant that only the first species mentioned in the list may be optionally substituted. The term optionally substituted when used herein means unsubstituted or substituted with a suitable group. Suitable groups will be known to the skilled person. Generally, such groups would not significantly detrimentally affect the function of the substituted group or of a larger moiety to which the substituted group is attached. In some cases, the skilled person would expect the substituent to improve the function of the substituted group. Preferably herein if substituted, the optional substituent is on atoms attached to atoms other than those directly bonded to the $C^a$ or $C^b$ carbon. Suitable substituent groups may for example be selected from —COOH, ester $OC(O)R^{10}$ or —$C(O)OR^{10}$, —$C(O)R^{19}$, ether —$OR^{15}$, epoxide, hydroxyl, boryl, boronic acid or ester, thiol, sulfonic acid, sulfonate ester, sulfonyl, sulfoxide, sulfinate, silyl, a silyl ether, a nitrile, cyanate or isocyanate, halide, nitro, imine, —$NCR^{13}R^{14}$, amine, —$R^{16}OR^{17}$, amido, $NR^9C(O)R^9$ or —$C(O)$—$NR^9(R^9)$, phosphinyl, phosphonic ester (—$P(O)(OR^{18})(OR^8)$ or —$OP(O)R(OR^{18})$) or acid (—$P(O)(OH)(OH)$), phosphate ester (—$OP(O)(OR^{18})(OR^8)$) and phosphoryl (—$P(O)R^{11}R^{12}$).

Groups $R^8$, $R^{11}$, $R^{12}$, $R^{13}$, $R^{14}$, $R^{18}$ and $R^{19}$ can be a hydrogen, an aliphatic, heteroaliphatic, alicyclic, heteroalicyclic, aryl or heteroaryl group as defined above. In certain embodiments $R^8$, $R^{11}$, $R^{12}$, $R^{13}$, $R^{14}$, $R^{18}$ and $R^{19}$ are each unsubstituted aliphatic, alicyclic or aryl.

Preferably, $R^8$, $R^{11}$, $R^{12}$, $R^{13}$, $R^{14}$, $R^{18}$ and $R^{19}$ are each hydrogen, methyl, ethyl, propyl or phenyl.

An amido group is preferably —$NR^9C(O)R^9$ or —$C(O)$—$NR^9(R^9)$ wherein $R^9$ can be hydrogen, an aliphatic, heteroaliphatic, alicyclic, heteroalicyclic, aryl or heteroaryl group as defined above. In certain embodiments, $R^9$ is unsubstituted aliphatic, alicyclic or aryl. Preferably $R^9$ is hydrogen, methyl, ethyl, propyl or phenyl. The amido group may be terminated by hydrogen, an aliphatic, heteroaliphatic, alicyclic, heteroalicyclic, aryl or heteroaryl group.

An ester group is preferably —$OC(O)R^{10}$ or —$C(O)OR^{10}$ wherein $R^{10}$ can be hydrogen, an aliphatic, heteroaliphatic, alicyclic, heteroalicyclic, aryl or heteroaryl group as defined above. In certain embodiments, $R^{10}$ is unsubstituted aliphatic, alicyclic or aryl. Preferably $R^{10}$ is hydrogen, methyl, ethyl, propyl or phenyl. The ester group may be terminated by hydrogen, an aliphatic, heteroaliphatic, alicyclic, heteroalicyclic, aryl or heteroaryl group.

An ether group is preferably —$OR^{15}$ or —$R^{16}OR^{17}$ wherein $R^{15}$, $R^{16}$ and $R^{17}$ can be an aliphatic, heteroaliphatic, alicyclic, heteroalicyclic, aryl or heteroaryl group as defined above. In certain embodiments, $R^{15}$, $R^{16}$ and $R^{17}$ each unsubstituted aliphatic, alicyclic or aryl. Preferably, $R^{15}$, $R^{16}$ and $R^{17}$ are each methyl, ethyl, propyl or phenyl. The ether group may be terminated by hydrogen, an aliphatic, heteroaliphatic, alicyclic, heteroalicyclic, aryl or heteroaryl group.

The aliphatic, aryl, araliphatic, aliphaticaryl, heteroaliphatic, heteroaryl, heteroaraliphatic, and heteroaliphaticaryl groups herein may also be optionally substituted with a carbonyl group, preferably in the form of a ketone group; or an hydroxyl group. In particular the groups of Formula I and/or Formula II. For the avoidance of doubt the carbonyl group carbon, or a heteroatom may, if represented as terminal in $R^2$ to $R^6$ be the linking atom in a composite structure. The stabilisers of the present invention may comprise more than one carbon-bonded labile hydrogen atom capable of being donated to a methacrylamide derivative capable of reaction with said labile hydrogen atom under the conditions in concentrated sulphuric acid medium. For example Tocopherol contains a labile hydrogen atom bonded to a carbon in a bicyclic structure and several labile hydrogen atoms bonded to carbons in a branched aliphatic chain attached to the bicyclic structure. Suitably, the stabiliser comprises between 1 and 20 carbon-bonded labile hydrogen atoms capable of being donated to a methacrylamide derivative capable of reaction with said labile hydrogen atom under the conditions in concentrated sulphuric acid medium, such as between 1 and 15 carbon-bonded labile hydrogen atoms or between 1 and 10 carbon-bonded labile hydrogen atoms, or between 1 and 6 carbon-bonded hydrogen atoms. The stabiliser may comprise between 2 and 20 carbon-bonded labile hydrogen atoms, such as between 3 and 20 carbon-bonded labile hydrogen atoms or between 4 and 20 or 5 and 20 carbon-bonded labile hydrogen atoms. In preferred embodiments of the present invention, the stabilisers comprise 2, 3, 4, 5, 6, 7, 8, 9, 10, 11, 12, 13, 14, 15, 16, 17, 18, 19 or 20, labile hydrogen atoms. In other preferred embodiments of the present invention, the stabilisers may comprise labile hydrogens attached to tertiary carbons. There may be 1 or more such labile hydrogens, for example between 1 and 6, such as at least 1, 2, 3, 4, 5 or 6 labile hydrogens attached to tertiary carbons.

Accordingly, in Formula I the substituents $R^2$-$R^6$ may themselves contain 1 or more further labile hydrogens.

Suitably, the stabiliser contains at least 9 carbon and/or sulphur atoms, preferably at least 9 carbon atoms, such as at least 10 carbon and/or sulphur atoms, preferably at least 10 carbon atoms. The stabiliser may contain up to 50 carbon atoms, up to 40 carbon atoms, up to 30 carbon atoms and especially up to 20 carbon atoms.

The stabilisers of the present invention according to Formula I may include all conformation isomers of compounds having more than one conformational isomer.

Stabilisers of the present invention may be, or be extracted from, natural products, one example of which is Vitamin E, also known as Tocopherol.

The method of the present invention may comprise two or more stabilisers, preferably according to one or more stabilisers according to Formula I. The stabilisers of the present invention may also be a component in a mixture containing compounds that are not stabilisers according to the present invention.

The stabilisers of the present invention may be selected from one or more of the group consisting of an isoprenoid, such as squalane (also known as perhydrosqualene; 2,6,10, 15,19,23-hexamethyltetracosane; spinacane; and dodecahydrosqualane); 9,10-dihydroanthracene; adamantane; tert-dodecyl polysulfide; tetralin (1,2,3,4-Tetrahydronaphthalene); fluorene (α-diphenylenemethane); decalin; and 5,12-dihydrotetracene; dihydrocoumarin; anthrone; squalene; hemisqualane; camphor; 4-methylnonane, triacontane; vitamin E (also known as tocopherol, including all four optical isomers); bicyclohexyl; petroleum diesel (also known as petrodiesel, automotive fuel); butyl cyclohexane; and decane. The petroleum diesel may be formed of a mixture of $C_{10}$ to $C_{15}$ hydrocarbons, and may be made up of about 75 wt % n, iso and/or cyclic hydrocarbons, which may be saturated or unsaturated and may comprise branching; with about 25 wt % aromatic hydrocarbons, wherein "about" may be defined as +/−25%. The average chemical formula for the petroleum diesel mixture may be between $C_{10}H_{20}$ to $C_{15}H_{28}$, such as $C_{12}H_{23}$.

Preferably, the stabiliser is selected from one or more of the group consisting of 9,10-dihydroanthracene; squalane; anthrone; hemisqualane; camphor; 4-methylnonane; tocopherol; petroleum diesel; decane and tert-dodecyl polysulfide.

The method of the present invention may comprise the stabiliser in any suitable amount. The upper limit for the amount of stabiliser in the reaction mixture may be considered to be the amount able to be solvated in the reaction mixture. Suitably, the stabiliser is present in the reaction mixture in an amount of ≥0.005% w/w, such as 0.01% w/w, or ≥0.03% w/w.

In the present invention, a methacrylamide derivative capable of reaction with the said labile hydrogen atom may be defined as methacrylamide derivative having at least one atom with at least one unpaired valence electron. The methacrylamide derivative may be a radical of methacrylamide; or a species formed from methacrylamide or its hydrolysis product methacrylic acid, for example a methacrylamide or methacrylic acid derived dimer, oligomer or polymer. Said species formed from methacrylamide may be methacrylamide, or a methacrylamide-containing dimer, oligomer or polymer, substituted with one or more of a sulphonate and/or sulphate group.

The term composite group may be defined as a group having at least one direct bond between the respective R groups with typically the resulting loss of hydrogen atoms from each of the respective atoms forming the said bond. For the avoidance of doubt, the direct bond is in addition to the indirect bond that is formed between the groups when they are bonded to $C^\alpha$.

Heteroatoms of the composite group may be in the form of an ether group; if a substituent, a hydroxyl group; an amine or amide, more preferably, a secondary amine, such as a secondary amine in a ring; nitrogen, sulphur and oxygen heterocycles; and/or a polysulphide group in the carbon backbone, such as a polysulphide containing at least three sulphur atoms. For example, an oxygen atom on a heteroalkyl R group may be directly bonded to a carbon atom of an aryl R group such that the oxygen is an interrupting heteroatom in the composite group. Such a group may thus be in the form of a composite group interrupted by a heteroatom in the form of an ether group or amino group a carbonyl group; carboxyl group.

Most preferred are composite group heteroatoms present as oxygen and nitrogen containing heterocycles, sulphur containing chains or carbonyl substituent oxygen atoms. Such heteroatom-containing groups have been found in particular to be stable. Preferably, a heteroatom is not directly bonded to the $C^\alpha$ atom, more suitably a heteroatom is spaced by at least two carbon atoms from the $C^\alpha$ atom.

The chemical environment of the amide stage of the ACH process is unique among the processes used to form MMA and MAA as it is highly acidic and non-aqueous as a result of the concentrated sulphuric acid solvent, the elevated temperatures, relatively long residence times, and the absence of dissolved oxygen. It has been found that other commercially available families of inhibitor compounds that are effective against polymerisation of acrylic monomers are not suitable under the conditions of the ACH process. The absence of oxygen to act as a co-inhibitor, and/or irreversible chemical degradation and/or chemical inactivity have been found to occur.

Advantageously, it has surprisingly been found that stabilisers of the present invention achieve reduction of tar build-up, thereby reducing blockages of the reaction vessels, process equipment, pipework, spray guns or other parts. In general, the hydrocarbon family is understood to be relatively unreactive. It is therefore surprising that the stabilisers of the present invention are effective specifically as stabilisers in the difficult conditions found in the amide stage of the ACH process.

Further advantageously, the stabilisers of the present invention have not been found to take part in any significant undesirable side-reactions with the other components that are present during the ACH process, nor have they been found to decompose in such a way that the product of the process becomes contaminated with a new trace impurity, or cause the reaction mix to foam, or cause corrosion or other damage to the process equipment.

Many of the compounds that make up the stabilisers of the present invention are relatively cheap and freely available, and in some cases will be components of complex mixtures of hydrocarbons that exist as process streams in the refining of oil. As such, the stabilisers are cost effective. Further, because the stabilisers can be obtained from multiple manufacturers/suppliers, the supply chain for subsequent operation is relatively reliable.

In the method of the present invention the stabilisers are typically introduced into the reaction medium in such a way as to allow it to be well mixed in with other components.

Preferably, the stabilisers are added to the process in the form of liquid, or a solution. This enables straightforward and accurate dosing of relatively small flows of stabiliser by using for example metering pumps.

The thorough mixing in of the stabiliser within the reaction vessel may be achieved by addition as a component of one of the feedstreams, by separate addition to the reaction medium, which is stirred vigorously, or a via an in-line static mixer used to facilitate introduction of one of the other incoming process streams. As the liquids within the amide stage vessels are typically turbulent in nature, it is relatively facile to introduce all flows in such a way that they become well mixed in the reaction medium vessel in a relatively short period of time.

For a better understanding of the invention, and to show how embodiments of the same may be carried into effect, reference will now be made, by way of example, to the following experimental data.

EXAMPLES

The effectiveness of a wide range of stabiliser compounds according to the invention for the amide stages of the ACH route to methacrylate monomers was measured by observing the concentration of MAM remaining after 30 minutes of exposure to a temperature of 160° C.

See Table 1 for a complete list of all the inventive and comparative compounds tested, as well as the results.

To measure the effectiveness of the compounds, they were each tested by making up a solution of methacrylamide (1% w/w) plus stabiliser compound (0.1% w/w), in deutero sulphuric acid ($D_2SO_4$). Handling operations were carried out in a nitrogen filled glove box in order to eliminate uptake of moisture and oxygen, as in practise the amide process steps in the ACH route to methacrylate monomers are carried out under an inert or reducing gas atmosphere. Eight, 5 mm diameter high pressure nmr tubes were then filled with the solution, before the tubes were sealed by securely adding gas tight screw caps. The tubes were removed from the nitrogen atmosphere, and seven were placed in an oil bath, with the temperature of the oil set at 160° C. Six of the tubes were removed one at a time at ten minute intervals over a period of 60 minutes, followed by a final seventh tube at 90 minutes and each cooled immediately after removal by immersion in water at ambient temperature thus generating a set of solutions that had been exposed to 160° C. temperature for varying lengths of time. $^1$Hnmr spectra were collected directly on the tubes at ambient temperature, and with the solutions remaining unexposed to air. It was possible to resolve and integrate peaks due to methacrylamide. By conducting the experiments in this way it was possible to produce a graph showing the extent of decomposition of Methacrylamide vs. time for each candidate compound. If the points making up the graph showed a regular curve pattern this was taken as an indication that the quality of the data was good, before selecting out the value at 30 minutes as a means of comparing the effectiveness of the candidate compounds. By comparison of the results to comparative examples 1 (no stabiliser present) and 2 (well known prior art stabiliser PTZ), the effectiveness of the respective stabilisers can be displayed, as shown in Table 1.

TABLE 1

Results

| | Stabiliser | Structure | % MAM Remaining after 30 minutes at 160° C. |
|---|---|---|---|
| Comparative example 1 | None | n/a | 18.0 |
| Comparative Example 2 | Phenothiazine (PTZ) | 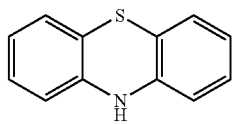 [SMILES: c1ccc2c(c1)Nc1ccccc1S2] | 75.4 |
| Example 1 | 9,10-Dihydroanthracene | 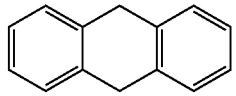 | 84.4, |

TABLE 1-continued

| | Stabiliser | Structure | % MAM Remaining after 30 minutes at 160° C. |
|---|---|---|---|
| Example 2 | 1,2,3,4-Tetrahydro-quinoline | 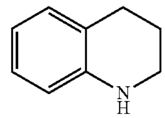 | 76.5 |
| Example 3 | Anthrone | 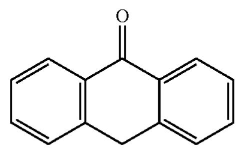 [SMILES: O=C1c2ccccc2Cc2ccccc21] | 81.8 |
| Example 4 | Squalane (2,6,10,15,19,23-Hexamethyl-tetracosane) | 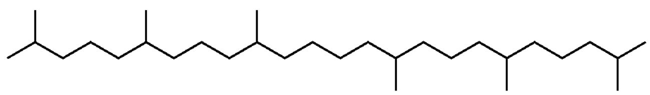 [SMILES: CC(C)CCCC(C)CCCC(C)CCCCC(C)CCCC(C)CCCC(C)C] | 95.7 |
| Example 5 | Hemisqualane | $C_{15}$ half length version of Squalane, with three C—H labile hydrogen sites | 89.3 |
| Example 6 | Camphor (R and S Camphor) | 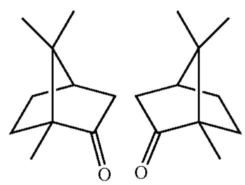 | 82.4 |
| Example 7 | 4-methylnonane | 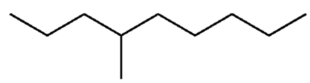 | 81.4 |
| Example 8 | Adamantane | 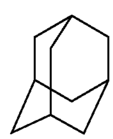 | 76.0 |
| Example 9 | Triacontane | 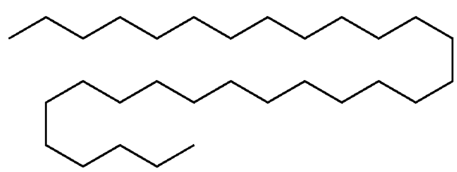 [SMILES: CCCCCCCCCCCCCCCCCCCCCCCCCCCCCC] | 75.5 |
| Example 10 | Vitamin E (Tocopherol, mixture of all four possible optical isomers) | 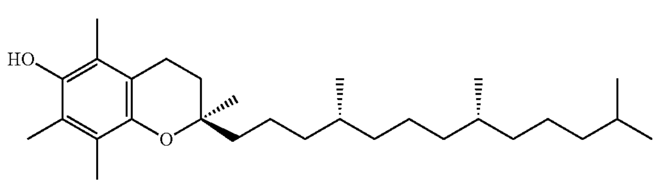 [SMILES: Cc1c(C)c2c(c(C)c1O)CC[C@@](C)(CCC[C@H](C)CCC[C@H](C)CCCC(C)C)O2] | 81.8 |
| Example 11 | Petroleum diesel* (aka petrodiesel, automotive fuel) | | 84.6 |

TABLE 1-continued

Results

| | Stabiliser | Structure | % MAM Remaining after 30 minutes at 160° C. |
|---|---|---|---|
| Example 12 | n-Decane | (zigzag structure of n-decane) | 84.0 |
| Example 13 | Tert-Dodecyl Polysulfide, No. S atoms per molecule x = 3 | $\left[ C_9H_{19}-C(CH_3)_2-S_x \right]_2$ | 92.9 |

*Mixture of $C_{10}$ to $C_{15}$ Hydrocarbons, made up of approximately 75% n, iso and cyclic saturated hydrocarbons, plus 25% aromatic hydrocarbons. The average chemical formula for the mixture is $C_{12}H_{23}$, ranging from $C_{10}H_{20}$ to $C_{15}H_{28}$. Hydrocarbons have varying levels of unsaturation and branching.

In comparative example 1 MAM is shown to breakdown in the presence of concentrated sulphuric acid thereby providing a cause of tar build-up. The examples according to the present invention show superior stabiliser benefits over the known stabiliser PTZ.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method of reducing polymer tar build-up in the production of methyl methacrylate and/or methacrylic acid by an acetone cyanohydrin (ACH) process comprising an amide stage reaction medium, wherein a stabilizer is contacted with the amide stage reaction medium, which stabilizer includes a hydrocarbon moiety capable of donating a labile hydrogen atom to a methacrylamide derivative capable of reaction with said labile hydrogen atom under the conditions in the amide stage reaction medium, wherein the stabilizer is selected from one or more of the group consisting of an isoprenoid, 9,10-dihydroanthracene; adamantane; tert-dodecyl polysulfide; tetralin; fluorene; decalin; and 5,12-dihydrotetracene; dihydrocoumarin; anthrone; squalene; hemisqualane; camphor; 4-methylnonane; triacontane; bicyclohexyl; petroleum diesel; butyl cyclohexane; and decane.

2. A method of producing methyl methacrylate or methacrylic acid comprising the steps of:
   a. contacting acetone cyanohydrin (ACH) with an excess of concentrated sulphuric acid to produce a mixture of sulphatoisobutyramide (SIBAM), hydroxyisobutyramide (HIBAM) and optionally methacrylamide; and
   b. thermally converting SIBAM and/or HIBAM to methacrylamide in concentrated sulphuric acid medium; and
   c. contacting the methacrylamide with water or with water and methanol;
   wherein a stabilizer is present during step b, which stabilizer is added as a hydrocarbon moiety capable of donating a labile hydrogen atom to a methacrylamide derivative capable of reaction with said labile hydrogen atom under the conditions in the said medium, wherein the stabilizer is selected from one or more of the group consisting of an isoprenoid, 9,10-dihydroanthracene; adamantane; tert-dodecyl polysulfide; tetralin; fluorene; decalin; and 5,12-dihydrotetracene; dihydrocoumarin; anthrone; squalene; hemisqualane; camphor; 4-methylnonane; triacontane; bicyclohexyl; petroleum diesel; butyl cyclohexane; and decane.

3. The method according to claim 1, wherein the stabilizer includes a hydrocarbon moiety capable of donating a labile hydrogen atom to a methacrylamide derivative capable of reaction with said labile hydrogen atom under the conditions in concentrated sulphuric acid medium.

4. The method according to claim 1, wherein the stabilizer is a hydrogen transfer agent that is operable to take part in a hydrogen atom transfer reaction under the conditions found in the amide stage of the ACH process wherein a hydrogen atom is transferred to a chemically reactive species in the same medium and in so doing prevents some or all of the side reactions that the species could otherwise take part in.

5. The method according to claim 1, wherein the stabilizer is selected from one or more of the group consisting of 9,10-dihydroanthracene; squalane; anthrone; hemisqualane; camphor; 4-methylnonane; petroleum diesel; decane and tert-dodecyl polysulfide.

6. The method according to claim 1, wherein the stabilizer is present in the reaction mixture in an amount of ≥0.005% w/w.

7. The method according to claim 1, wherein a concentrated sulphuric acid medium in which the stabilizer is capable of donating a labile hydrogen atom to a methacrylamide derivative is in the form of the amide stage reaction medium.

* * * * *